United States Patent
Yu et al.

(10) Patent No.: US 10,311,168 B2
(45) Date of Patent: Jun. 4, 2019

(54) METHOD AND SYSTEM FOR RIGHT-SIZING FUNCTION-SPECIFIC BLOCKS IN A HEALTHCARE BUILDING WITH A GIVEN ARCHITECTURAL PARTI TO SUPPORT A SPECIFIC SPACE PROGRAM

(71) Applicant: Aditazz, Inc., Brisbane, CA (US)

(72) Inventors: Robert Yu, Fremont, CA (US); Sudha Hajela, Brisbane, CA (US); John Victor-Faichney, Brisbane, CA (US)

(73) Assignee: ADITAZZ, INC., Brisbane, CA (US)

( * ) Notice: Subject to any disclaimer, the term of this patent is extended or adjusted under 35 U.S.C. 154(b) by 335 days.

(21) Appl. No.: 15/245,817

(22) Filed: Aug. 24, 2016

(65) Prior Publication Data

US 2017/0061340 A1    Mar. 2, 2017

Related U.S. Application Data

(60) Provisional application No. 62/209,299, filed on Aug. 24, 2015.

(51) Int. Cl.
| | |
|---|---|
| *G06F 17/50* | (2006.01) |
| *G06Q 10/06* | (2012.01) |
| *G06Q 50/22* | (2018.01) |
| *G06F 19/00* | (2018.01) |

(52) U.S. Cl.
CPC .......... *G06F 17/5004* (2013.01); *G06F 17/50* (2013.01); *G06F 19/00* (2013.01); *G06Q 10/0633* (2013.01); *G06Q 50/22* (2013.01)

(58) Field of Classification Search
CPC combination set(s) only.
See application file for complete search history.

(56) References Cited

U.S. PATENT DOCUMENTS

| | | | |
|---|---|---|---|
| 2002/0032546 A1* | 3/2002 | Imamura | G06Q 30/0601 703/1 |
| 2010/0198563 A1* | 8/2010 | Plewe | G06F 17/5004 703/1 |
| 2011/0082638 A1* | 4/2011 | Khorashadi | G01C 21/20 701/532 |

(Continued)

OTHER PUBLICATIONS

Nethercote et al., "MiniZinc: Towards a Standard CP Modelling Language" (2007), International Conference on Principles and Practice of Constraint Programming CP 2007, pp. 529-543 [retrieved from https://link.springer.com/content/pdf/10.1007%2F978-3-540-74970-7.pdf].*

(Continued)

*Primary Examiner* — Brian W Wathen

(57) ABSTRACT

A computer-implemented method for right-sizing function-specific blocks in a healthcare building with a given architectural parti to support a specific space program is disclosed. In an embodiment, the method involves describing the relative locations of function-specific blocks using a coordinate system, wherein the function-specific blocks are placed in particular locations within the building relative to a circulation pattern, describing constraints related to the areas of the function-specific blocks, and adjusting the areas and/or aspect ratios of the function-specific blocks to find a solution that maintains the relative locations of the function-specific blocks while meeting the area constraints.

20 Claims, 16 Drawing Sheets

(56) References Cited

U.S. PATENT DOCUMENTS

| | | |
|---|---|---|
| 2012/0239353 A1 | 9/2012 | Vercruysse et al. |
| 2013/0289945 A1 | 10/2013 | Ball et al. |
| 2014/0052416 A1* | 2/2014 | Yu .................. G06F 17/5004 703/1 |
| 2014/0095122 A1 | 4/2014 | Appleman |
| 2014/0214368 A1 | 7/2014 | Loberg |

OTHER PUBLICATIONS

Michalek et al., "Architectural Layout Design Optimization" (2002), Eng. Opt., vol. 34(5), pp. 461-484 [retrived from https://www.cmu.edu/me/ddl/publications/2002-Michalek,Choudhary,Papalambros-EO-ArchLayout.pdf].*

International Search Report, PCT/US2016/048400, dated Oct. 31, 2016.

* cited by examiner

PROGRAM SUMMARY - TABLE 1

*EMERGENCY*

| EMERGENCY | BEDS/ROOM | DGSF |
|---|---|---|
| CLINICAL CARE | 60 | 36,668 |

*SUPPORT*

| ADMINISTRATION AND PUBLIC | BEDS/ROOM | DGSF |
|---|---|---|
| ENTRY AREA | - | 5,755 |
| ADMITTING | - | 2,801 |
| ADMINISTRATION | - | 621 |
| | | |
| AUXILIARY SUPPORT | | |
| MATERIAL MANAGEMENT | - | 8,250 |
| MESSENGER/MAILROOM | - | 2,544 |
| ENVIRONMENTAL SERVICES | - | 1,295 |
| INFORMATION TECHNOLOGY | - | 2,731 |
| PBX | - | 719 |
| DIETARY | - | 828 |
| SUBTOTAL | | 25,544 |

| DGSF TOTAL | | 323,982 |
|---|---|---|
| CIRCULATION/EXTERIOR WALL | 18% | 58,317 |
| PLANT SERVICES | 9% | 34,407 |
| BGSF TOTAL | | 416,706 |

FIG. 3B

METHOD AND SYSTEM FOR RIGHT-SIZING FUNCTION-SPECIFIC BLOCKS IN A HEALTHCARE BUILDING WITH A GIVEN ARCHITECTURAL PARTI TO SUPPORT A SPECIFIC SPACE PROGRAM

BACKGROUND

Buildings are an integral part of everyday life. The process of planning, designing, and constructing buildings has evolved over several thousands of years. Today, the steps followed to physically realize modern buildings are very complicated and require a high degree of skilled labor that can span several different disciplines. This complexity poses a huge challenge in terms of time, money, and other resources expended in order to build a viable facility that can be used to deliver the intended services in an efficient and profitable way.

SUMMARY

In an embodiment, a computer-implemented method for right-sizing function-specific blocks in a healthcare building with a given architectural parti to support a specific space program is disclosed. In the embodiment, the method involves describing the relative locations of function-specific blocks using a coordinate system, wherein the function-specific blocks are placed in particular locations within the building relative to a circulation pattern, describing constraints related to the areas of the function-specific blocks, and adjusting the areas and/or aspect ratios of the function-specific blocks to find a solution that maintains the relative locations of the function-specific blocks while meeting the area constraints.

In a second embodiment, adjusting the areas and/or aspect ratios of the function-specific blocks comprises maintaining the circulation pattern.

In another embodiment, the function-specific blocks are placed in particular locations within the architectural parti of the building taking into account workflow of services that are provided within the function-specific blocks.

In another embodiment, describing the relative locations of function-specific blocks using a coordinate system involves identifying circulation elements and function-specific blocks with a handle and associating the handle with coordinates of corresponding vertices representing the area of the circulation elements and function-specific blocks.

In another embodiment, the handle is associated with a range of coordinates.

In another embodiment, the computer-implemented method further involves outputting the solution as x and y variables that translate directly to the positions, areas, and aspect ratios of function-specific blocks.

In another embodiment, the computer-implemented method further involves outputting a graphical depiction of the solution that includes the adjusted areas and/or aspect ratios.

In another embodiment, a computer-implemented method for right-sizing function-specific blocks in a healthcare building with a given architectural parti to support a specific space program is disclosed, In the embodiment, the method involves identifying knowns related to function-specific blocks that are placed in particular locations within a building relative to a circulation pattern, identifying unknowns related to the function-specific blocks as placed within the building relative to the circulation pattern, identifying constraints related to the function-specific blocks as placed within the building relative to the circulation pattern, and solving for the unknowns given the knowns and the constraints to adjust areas and/or aspect ratios of the function-specific blocks to find a solution that maintains the relative locations of the function-specific blocks while meeting the area constraints.

In another embodiment, adjusting the areas and/or aspect ratios of the function-specific blocks comprises maintaining the circulation pattern.

In another embodiment, the function-specific blocks are placed in particular locations within the architectural parti of the building taking into account workflow of services that are provided within the function-specific blocks.

In another embodiment, describing the relative locations of function-specific blocks using a coordinate system involves identifying circulation elements and function-specific blocks with a handle and associating the handle with coordinates of corresponding vertices representing the area of the circulation elements and function-specific blocks.

In another embodiment, adjusting the areas and/or aspect ratios of the function-specific blocks involves directing a solver to apply a particular space program to a previously modeled architectural parti having the same identified knowns.

In another embodiment, the previously modeled architectural parti is selected from a library that includes at least one previously modeled architectural parti for at least one department using at least one building floor plan.

In another embodiment, the computer-implemented method further involves outputting the solution as x and y variables that translate directly to positions, areas, and aspect ratios of function-specific blocks.

In another embodiment, the computer-implemented method further comprising outputting a graphical depiction of the solution that includes the adjusted areas and/or aspect ratios.

In another embodiment, a non-transitory computer readable medium that stores computer readable instructions, which when executed by at least one processor, implement a method for right-sizing function-specific blocks in a healthcare building with a given architectural parti to support a specific space program is disclosed. In the embodiment, the method involves describing relative locations of function-specific blocks using a coordinate system, wherein the function-specific blocks are placed in particular locations within a building relative to a circulation pattern, describing constraints related to areas of the function-specific blocks, and adjusting the areas and/or aspect ratios of the function-specific blocks to find a solution that maintains the relative locations of the function-specific blocks while meeting the area constraints.

In another embodiment, a computer-implemented right-sizing tool is disclosed. In the embodiment, the computer-implemented room placement tool includes at least one processor and a non-transitory computer readable medium that stores computer readable instructions, which when executed by at least one processor, implement a method for right-sizing function-specific blocks in a healthcare building with a given architectural parti to support a specific space program, the method involving describing relative locations of function-specific blocks using a coordinate system, wherein the function-specific blocks are placed in particular locations within a building relative to a circulation pattern, describing constraints related to areas of the function-specific blocks, and adjusting the areas and/or aspect ratios of the function-specific blocks to find a solution that maintains the relative locations of the function-specific blocks while meeting the area constraints.

In another embodiment, describing the relative locations of function-specific blocks and describing constraints related to the areas of the function-specific blocks can be performed by selecting a previously modeled architectural parti from a library.

In another embodiment, wherein the library includes previously modeled architectural parti for at least one department using at least one building floor plan.

In another embodiment, wherein adjusting the areas and/or aspect ratios of the function-specific blocks involves directing a solver to apply a particular space program to the selected previously modeled architectural parti.

Other aspects and advantages of embodiments of the present invention will become apparent from the following detailed description, taken in conjunction with the accompanying drawings, illustrated by way of example of the principles of the invention.

BRIEF DESCRIPTION OF THE DRAWINGS

FIGS. 3A and 3B are a table visualization of an exemplary space program for a hospital.

Throughout the description, similar reference numbers may be used to identify similar elements.

DETAILED DESCRIPTION

Figure 1A:
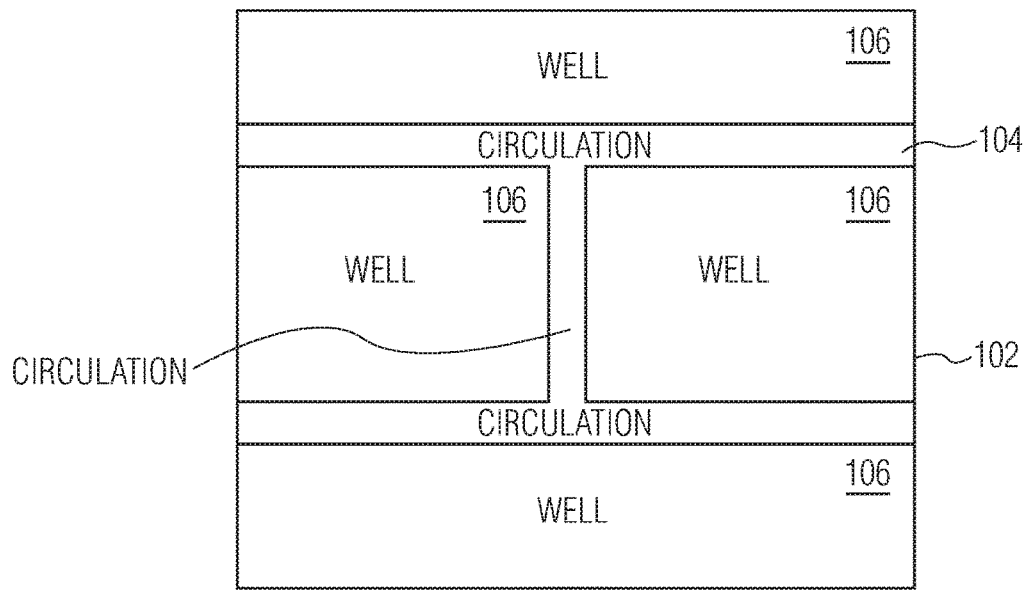
FIG. 1A depicts a building floor plan with an architectural parti that includes a rectangular perimeter and an "H" shaped circulation pattern.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

Buildings are an integral part of everyday life. Some buildings, such as healthcare facilities, are used to deliver complex multi-step services that utilize different spaces within the building for different functions. In order to efficiently deliver the desired services, it is important to have function-specific spaces that are spatially organized in a certain way within a building. Space planning during the design of a complex building is typically a labor-intensive process that is repeated anew for each new building design.

Building designs can be characterized by their architectural parti. As is known in the field, the architectural parti is typically the most basic organizational principle that expresses the architectural design. As used herein, the architectural parti or simply "parti" defines the basic shape of the building (e.g., the perimeter shape) and the corresponding circulation pattern within the building. For example, building partis for a healthcare facility may include a courtyard parti, a spine parti, and a spoke parti. A wide range of different partis are possible for buildings, including buildings within which healthcare services will be provided.

Given the manual nature of conventional space planning and the wide range of possible architectural partis, it can be a daunting task to prepare and evaluate space plans for complex buildings such as buildings within which healthcare services will be provided. As mentioned above, buildings may be designed to deliver complex multi-step services such as healthcare services. For example, healthcare buildings may be designed to provide a wide range of services, including services related to a general hospital, a surgical center, an outpatient medical office building, and a laboratory. For example, a large general hospital may require an inpatient function, a diagnostic and treatment function, an emergency function, and a support function. The type and volume of healthcare services to be delivered within a building will dictate the department blocks and the estimated square footage needs of each department block and of each specific block within a particular department. The selected architectural parti of a desired building will dictate possible locations at which function-specific blocks can be placed.

FIG. 1A depicts a building floor plan with an architectural parti that includes a rectangular perimeter 102 and an "H" shaped circulation pattern 104. With reference to FIG. 1A, circulation elements define the circulation pattern and the non-circulation spaces are referred to as "wells" 106. Function-specific blocks (e.g., departmental blocks of a specific department) are placed in the wells to produce a building floor plan. In an embodiment, a department (e.g., an operating room department) includes seven function-specific blocks including, for example, function-specific blocks A-G (e.g., admitting, general surgical, intensive care unit (ICU), neonatal intensive care unit (NICU), diagnostic and imaging, step-down recovery, and support). During the space planning process, the function-specific blocks are placed within the parti taking into account the workflow of the services that are provided within the function-specific blocks. For example, the workflow between the different function-specific blocks is an important factor in the desired locations of the function-specific blocks relative to each other.

Figure 1B:
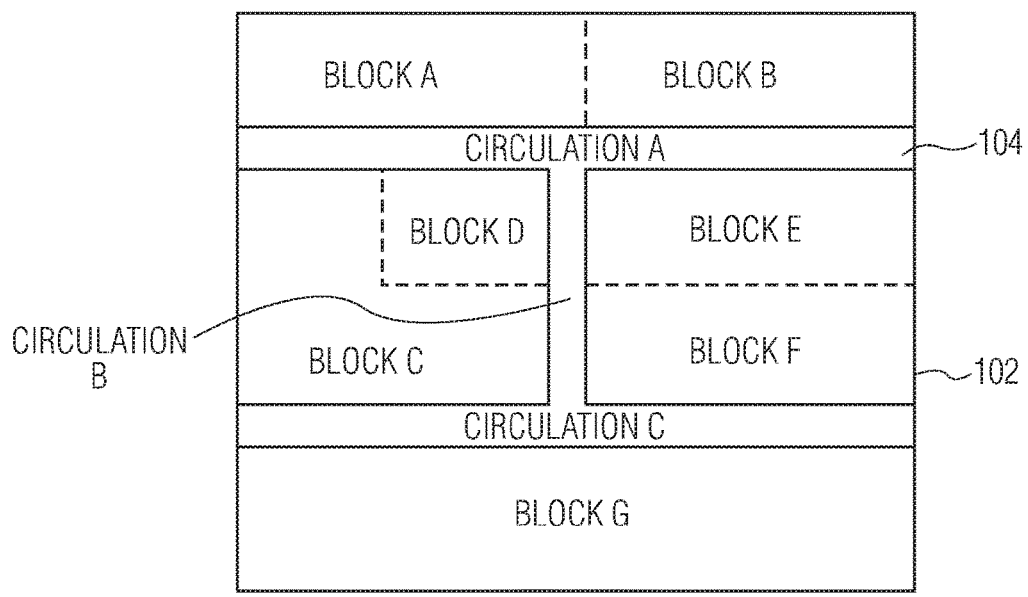
FIG. 1B depicts an example placement of function-specific blocks A-G within the building having the architectural parti as shown in FIG. 1A.

FIG. 1B depicts an example placement of function-specific blocks A-G within the building having the architectural parti as shown in FIG. 1A. In the embodiment of FIG. 1B, the function-specific blocks are placed without concern for the relative areas of the function-specific blocks and without concern for the aspect ratios of the function-specific blocks. The primary organizing principle of the block placement at this point is the workflow of the function-specific blocks given the architectural parti (e.g., given the shape of the building and the circulation pattern within the building). For example, the workflow of the operations performed within the building will make it desirable to have certain function-specific blocks in close proximity to each other.

Figure 2A:
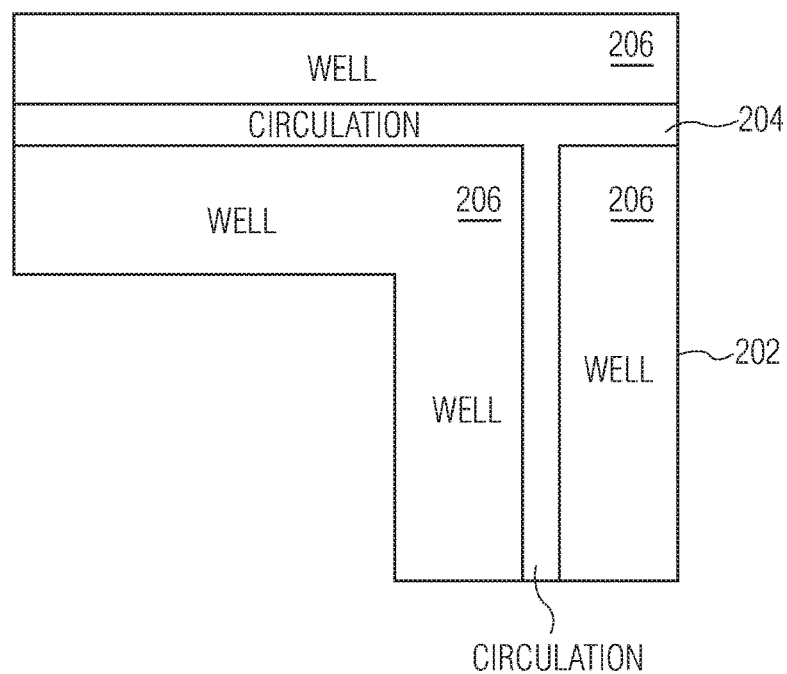
FIG. 2A depicts a building floor plan with a different architectural parti than shown in FIG. 1A.

FIG. 2A depicts a building floor plan with a different architectural parti. The architectural parti depicted in FIG. 2A includes a building with an "L" shaped perimeter 202 and a generally "L" shaped circulation pattern 204. With reference to FIG. 2A, circulation elements define the circulation pattern and the non-circulation spaces are referred to as "wells" 206. Function-specific blocks (e.g., departmental blocks of a specific department) are placed in the wells to produce a building floor plan. In an embodiment, a department (e.g., an operating room department) includes seven function-specific blocks including, for example, function-specific blocks A-G (e.g., admitting, general surgical, intensive care unit (ICU), neonatal intensive care unit (NICU), diagnostic and imaging, step-down recovery, and support). During the space planning process, the function-specific blocks are placed within the parti taking into account the workflow of the services that are provided within the function-specific blocks. For example, the workflow between the different function-specific blocks is an important factor in the desired locations of the function-specific blocks relative to each other.

Figure 2B:
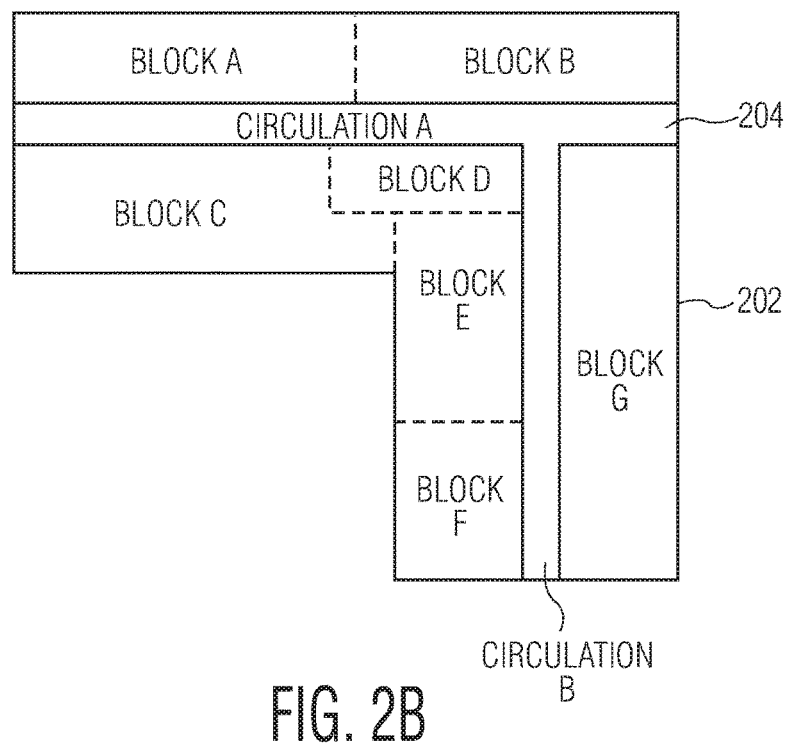
FIG. 2B depicts an example placement of function-specific blocks A-G within the building having the architectural parti as shown in FIG. 2A.

FIG. 2B depicts an example placement of function-specific blocks A-G within the building having the architectural parti as shown in FIG. 2A. In the embodiment of FIG. 2B, the function-specific blocks are placed without concern for the relative areas of the function-specific blocks and without concern for the aspect ratios of the function-specific blocks. The primary organizing principle of the block placement at this point is the workflow of the function-specific blocks given the architectural parti (e.g., given the shape of the building and the circulation pattern within the building).

Figure 3A:
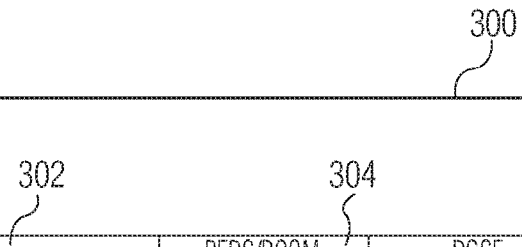

Given the architectural partis as shown in FIGS. 1A and 2A and the placement of function-specific blocks as shown in FIGS. 1B and 2B, there is a need to "right-size" the function-specific blocks given a particular space program, where a space program defines the square footage that is needed for each function-specific block. For example, a space program may specify a certain square footage that is needed for each of the function-specific blocks A-G shown in FIGS. 1B and 2B. FIGS. 3A and 3B are a table visualization 300 of an exemplary space program for a hospital. The table includes a column with names of function-specific blocks 302, a column with a corresponding number of beds/rooms (where appropriate) 304, and a column for the corresponding square footage of the function-specific blocks 306 (e.g., identified as Departmental Gross Square Footage (DGSF)).

With reference to FIGS. 1B and 2B, it is a complex multi-variable problem to fit all of the function-specific blocks into the designated locations with the desired areas (e.g., to right-size the function-specific blocks). In fact, in some cases it may not be possible to fit all of the function-specific blocks as specified by the space program into the building with the given parti. In any case, the problem can be extremely complex to solve using conventional techniques. For example, it can be quite difficult and time-consuming for an architectural planner to manually right-size multiple function-specific blocks within a given parti according to a desired space program.

In accordance with an embodiment of the invention, a computer-implemented technique for right-sizing function-specific blocks in a healthcare building with a given architectural parti to support a specific space program involves placing function-specific blocks in particular locations within the building, describing the relative locations of the function-specific blocks using a coordinate system, describing constraints related to the areas of the function-specific blocks and then adjusting the areas and/or aspect ratios of the function-specific blocks to find a solution that maintains the relative locations of the function-specific blocks while meeting the area constraints. In an embodiment, the right-sizing technique is implemented using a constraint-based approach that utilizes a constraint-based programming language. Using a constraint-based approach involves identifying certain knowns, identifying certain unknowns, and establishing a set of constraints. In an embodiment, the constraint-based approach is applied directly to the problem of right-sizing function-specific blocks in a healthcare building with a given architectural parti to support a specific space program.

Examples of the technique for right-sizing function-specific blocks in a healthcare building with a given architectural parti to support a specific space program are described below for the case of an operating room and for the case of a laboratory. Although example cases are described below, the technique for right-sizing function-specific blocks is applicable to other buildings within which healthcare services will be provided.

Operating Room Example

Figure 4A:
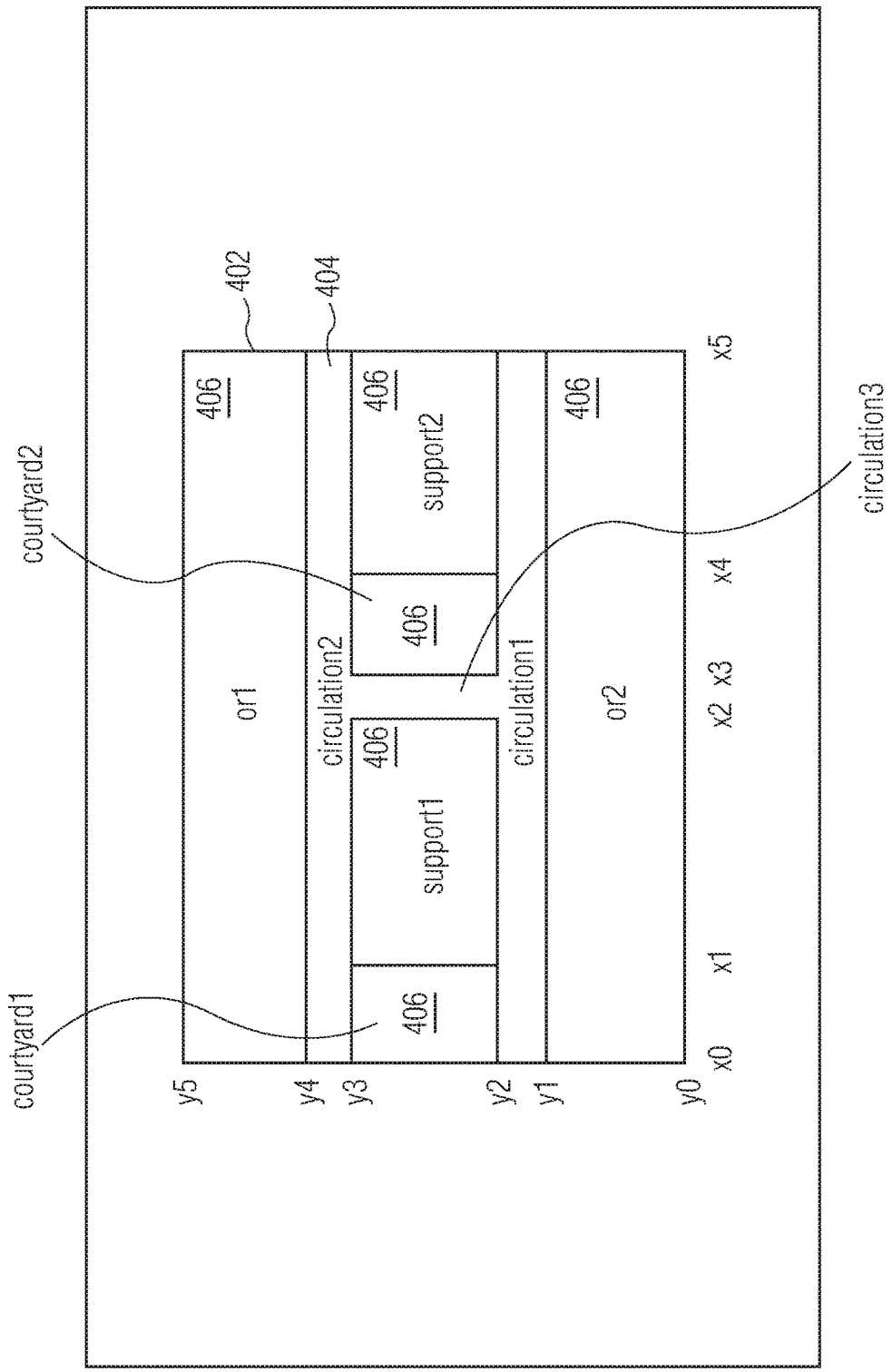
FIG. 4A depicts an example of a building floor plan with an architectural parti for an operating room (e.g., an operating room department that is typically referred to collectively as an "OR" or "operating room") that includes a rectangular perimeter and an "H" shaped circulation pattern.

FIG. 4A depicts an example of a building floor plan with an architectural parti for an operating room (e.g., an operating room department that is typically referred to collectively as an "OR" or "operating room") that includes a rectangular perimeter 402 and an "H" shaped circulation pattern 404. FIG. 4A also depicts the placement of function-specific blocks 406 within the building relative to the circulation pattern. As shown in FIG. 4A, circulation elements include circulation element 1 (e.g., a straight horizontally aligned hallway identified as "circulation1"), circulation element 2 (e.g., a straight horizontally aligned hallway identified as "circulation2"), and circulation element 3 (e.g., a straight vertically aligned hallway identified as "circulation3"). As shown, circulation element 3 connects circulation element 1 to circulation element 2. As shown in FIG. 4A, the function-specific blocks include an operating room block 1 (identified as "or1"), an operating room block 2 (identified as "or2"), a support block 1 (identified as "support1"), a support block 2 (identified as "support2"), a courtyard 1 (identified as "courtyard1"), and a courtyard 2 (identified as "courtyard2").

In an embodiment, the circulation elements and function-specific blocks are placed within the building floor plan manually by an architectural planner without concern for the actual area (e.g., in terms of square footage) of the circulation elements and of the function-specific blocks and without concern for the aspect ratios of the circulation elements and of the function-specific blocks. In an embodiment, the manual placement may be made by, for example, hand drawing and/or a basic drawing program. An important consideration of the architectural planner in the placement process is the workflow between the function-specific blocks. For example, in the case of FIG. 4A, the workflow makes it desirable to have both of the operating room blocks (or1 and or2) relatively close to the support blocks (support1 and support2) and desirable to have the courtyard blocks (courtyard1 and courtyard2) relatively close to the operating room blocks (or1 and or2). Traditionally, the architectural planner utilizes personal experience and knowledge about workflow to place the function-specific blocks within a given architectural parti.

Figure 4B:
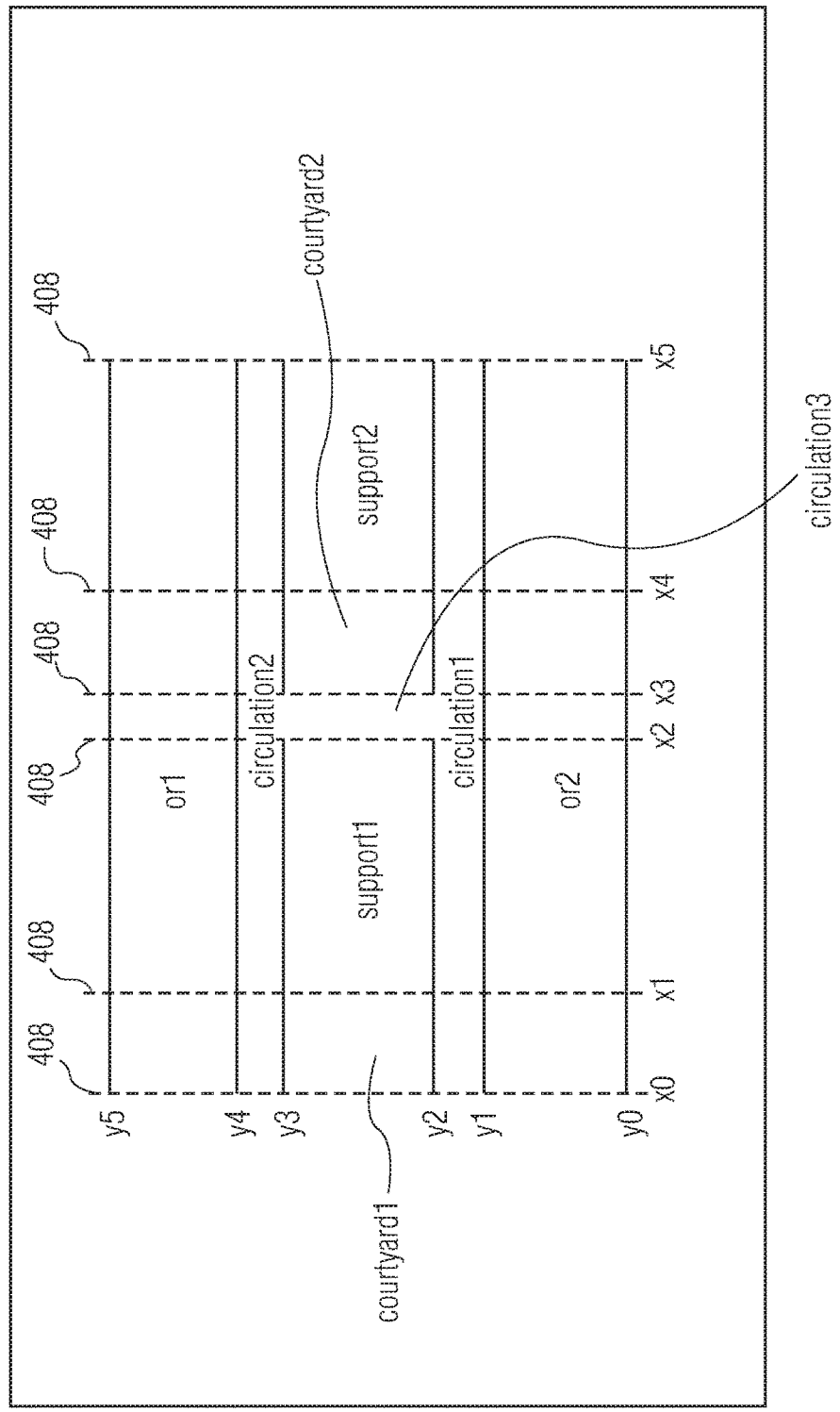
FIG. 4B illustrates the x-axis block edges that exist in the building floor plan of FIG. 4A.

Once the circulation elements and the function-specific blocks have been placed within the building floor plan, the relative locations of the circulation elements and the function-specific blocks are described using an x-y coordinate system. In an embodiment, a first step in the description process involves identifying each of the block edges along the x-axis, where edges exist at the vertical edge of any circulation element and at the vertical edge of any function-specific block. FIG. 4B illustrates the x-axis block edges 408 that exist in the building floor plan of FIG. 4A. As illustrated in FIG. 4B, the block edges along the x-axis are identified by dashed vertical lines and include edges at coordinates x0-x5.

At this point, the coordinates x0-x5 correspond to the block edges, but do not represent absolute values along the x-axis.

Figure 4C:
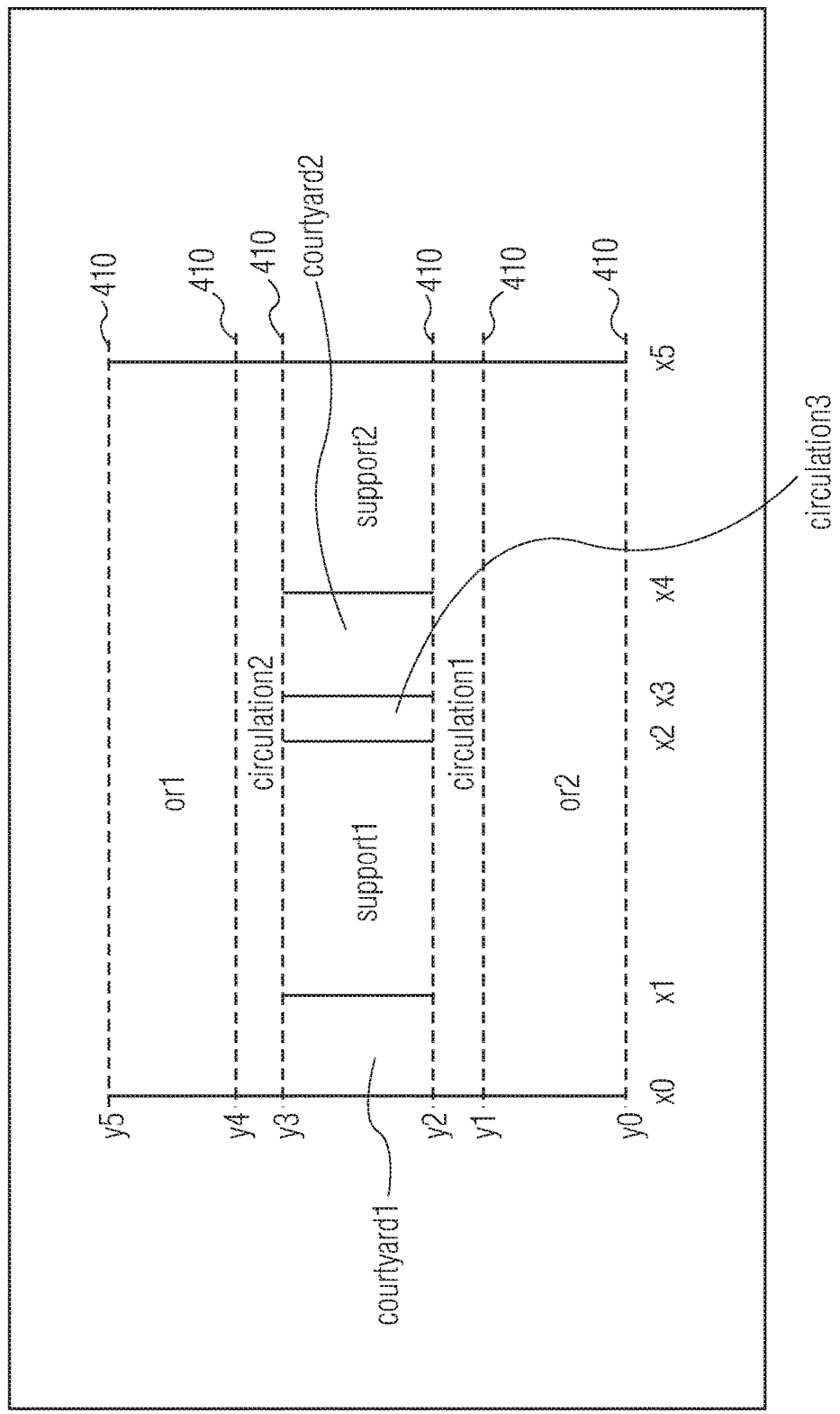
FIG. 4C illustrates the y-axis block edges 410 that exist in the building floor plan of FIG. 4A.

A next step in the description process involves identifying each of the block edges along the y-axis, where a block edge exists at the horizontal edge of any circulation element and at the horizontal edge of any function-specific block. FIG. 4C illustrates the y-axis block edges 410 that exist in the building floor plan of FIG. 4A. As illustrated in FIG. 4C, the block edges along the y-axis are identified by dashed horizontal lines and include edges at coordinates y0-y5. As with the x-axis, at this point, the coordinates y0-y5 correspond to the block edges, but do not represent absolute values along the y-axis.

The next step in the process involves describing the area of each circulation element and function-specific block using the coordinates of the identified block edges. In an embodiment, the process involves identifying circulation elements and function-specific blocks with a handle and associating the handles with coordinates of the corresponding vertices that represent the area of the respective circulation elements and function-specific blocks. For example, the area of the function-specific blocks of FIG. 4A are described as:

$$\text{area\_or1} = (x5-x0)*(y5-y4);$$

$$\text{area\_or2} = (x5-x0)*(y1-y0);$$

$$\text{area\_support1} = (x2-x1)*(y3-y2);$$

$$\text{area\_support2} = (x5-x4)*(y3-y2);$$

$$\text{area\_courtyard1} = (x1-x0)*(y3-y2); \text{ and}$$

$$\text{area\_courtyard2} = (x4-x3)*(y3-y2).$$

In an embodiment, the area of circulation elements and the function-specific blocks can also be constrained to a particular range or ranges. For example, the constrained area of function-specific blocks "courtyard1" and "courtyard2" can be constrained by the following description:

$$c\text{area\_courtyard1} >= \text{round}((1-\text{area\_tolerance})*\text{area\_courtyard1});$$

$$c\text{area\_courtyard1} <= \text{round}((1-\text{area\_tolerance})*\text{area\_courtyard1});$$

$$c\text{area\_courtyard2} >= \text{round}((1-\text{area\_tolerance})*\text{area\_courtyard2});$$

$$c\text{area\_courtyard2} <= \text{round}((1-\text{area\_tolerance})*\text{area\_courtyard2});$$

where the tolerance can be pre-set (e.g., area_tolerance=0.0800).

Additional constraints may be set such as:

maximum x dimension (e.g., xmax=x5);

maximum y dimension (e.g., ymax=y5);

constraints on relative positions of x and y vertices, such as:

$$x0 < x1;$$

$$x1 < x2;$$

$$x2 < x3;$$

$$x3 < x4;$$

$$x4 < x5;$$

$$y0 < y1;$$

$y1 \leq y2;$ $y2 \leq y3;$ $y3 \leq y4;$ and $y4 \leq y5.$

In an embodiment, the specifics of a particular building floor plan are modeled using a constraint-based programming language such as "MiniZinc" and stored in a file such as an ".mzn" file. In an embodiment, a base or generic parti can be modeled and stored in a base .mzn file and custom information for a specific parti can be modeled and stored in a custom .mzn file. In the embodiment of FIG. 4A, custom constraints may include specific bay sizes (e.g., bay_x=8400, bay_y=8400), special constraints on the courtyards (e.g., area_courtyard1=area_courtyard2), special constraints on the support areas (e.g., area_support1=area_support2), special constraints on the depth of the operating room blocks (e.g., y5-y4=9100 and y1-y0=9100, and constraints on the y dimensions (e.g., y5-y0=4*bay_y, where "bay_y" is the y dimension of a bay in the building).

In an embodiment, the custom constraints file also includes a space program that identifies area requirements of some of the function-specific blocks.

With the desired knowns, unknowns, and constraints identified, the problem can be solved using an existing solver engine. In an embodiment, two different runs, run1 and run2, are provided using the same architectural parti. In run1, the bay size is set to 8.4 m and the circulation corridors are set to a width of 2.4 m and in run2, the bay size is set to 9.1 m and the circulation corridors are set to a width of 1.8 m. Outputs of the solutions are stored in a .yaml file.

Figure 4D:
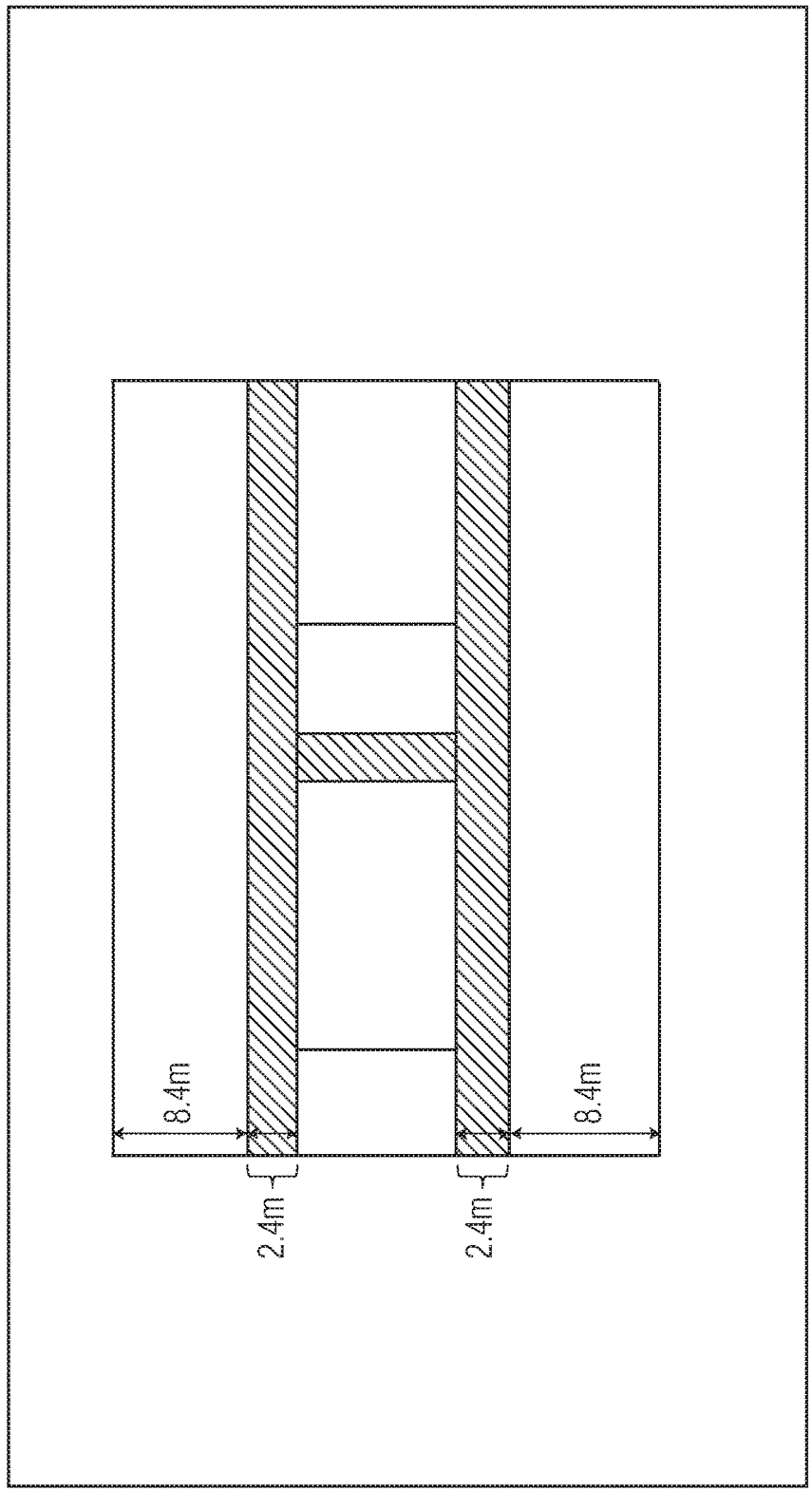
FIG. 4D is a graphical depiction of the run1 result as a floor plan layout.

FIG. 4D is a graphical depiction of the run1 result as a floor plan layout.

Figure 4E:
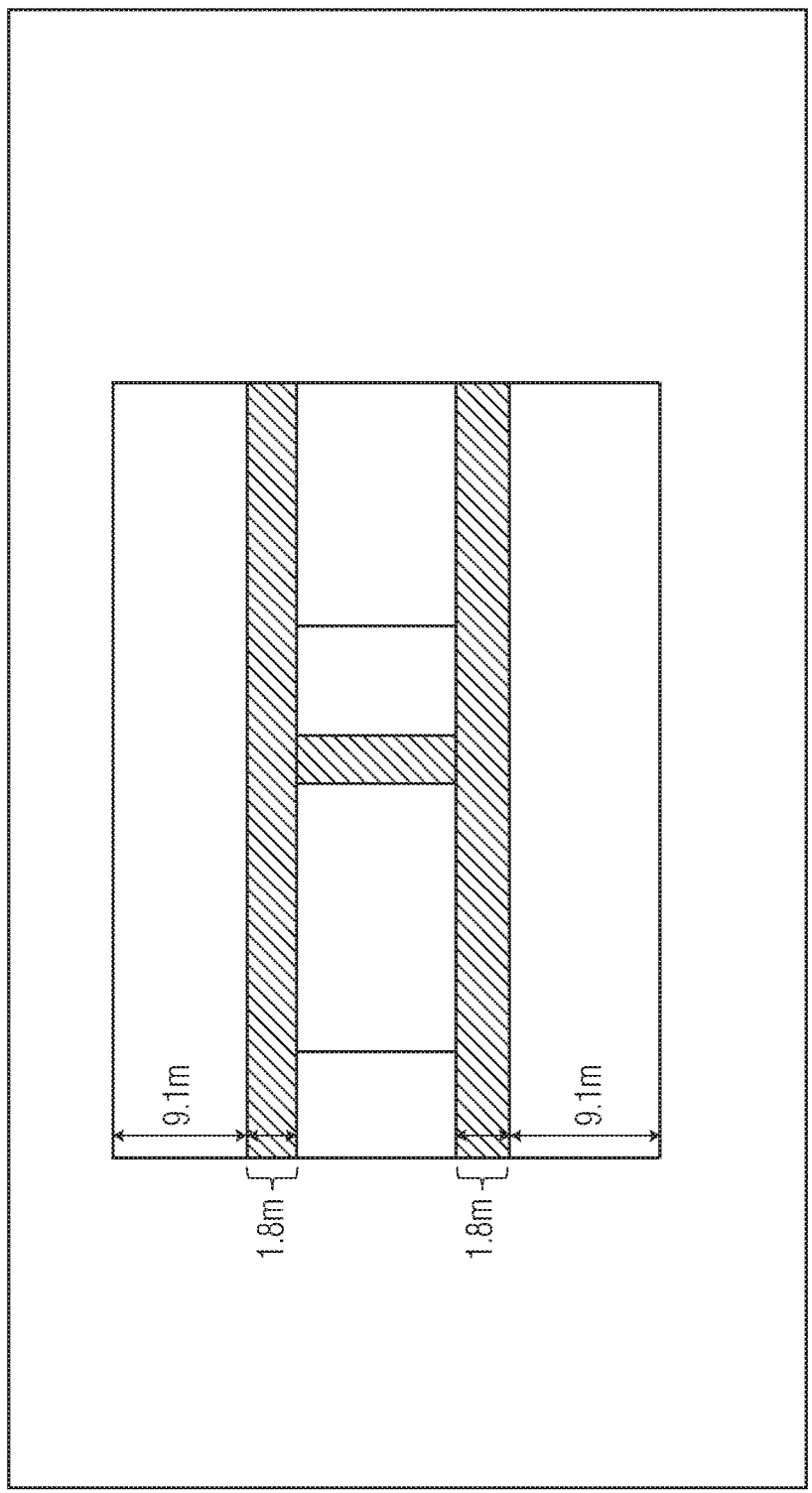
FIG. 4E is a graphical depiction of the run2 result as a floor plan layout.

FIG. 4E is a graphical depiction of the run2 result as a floor plan layout.

Laboratory Example

Figure 5A:
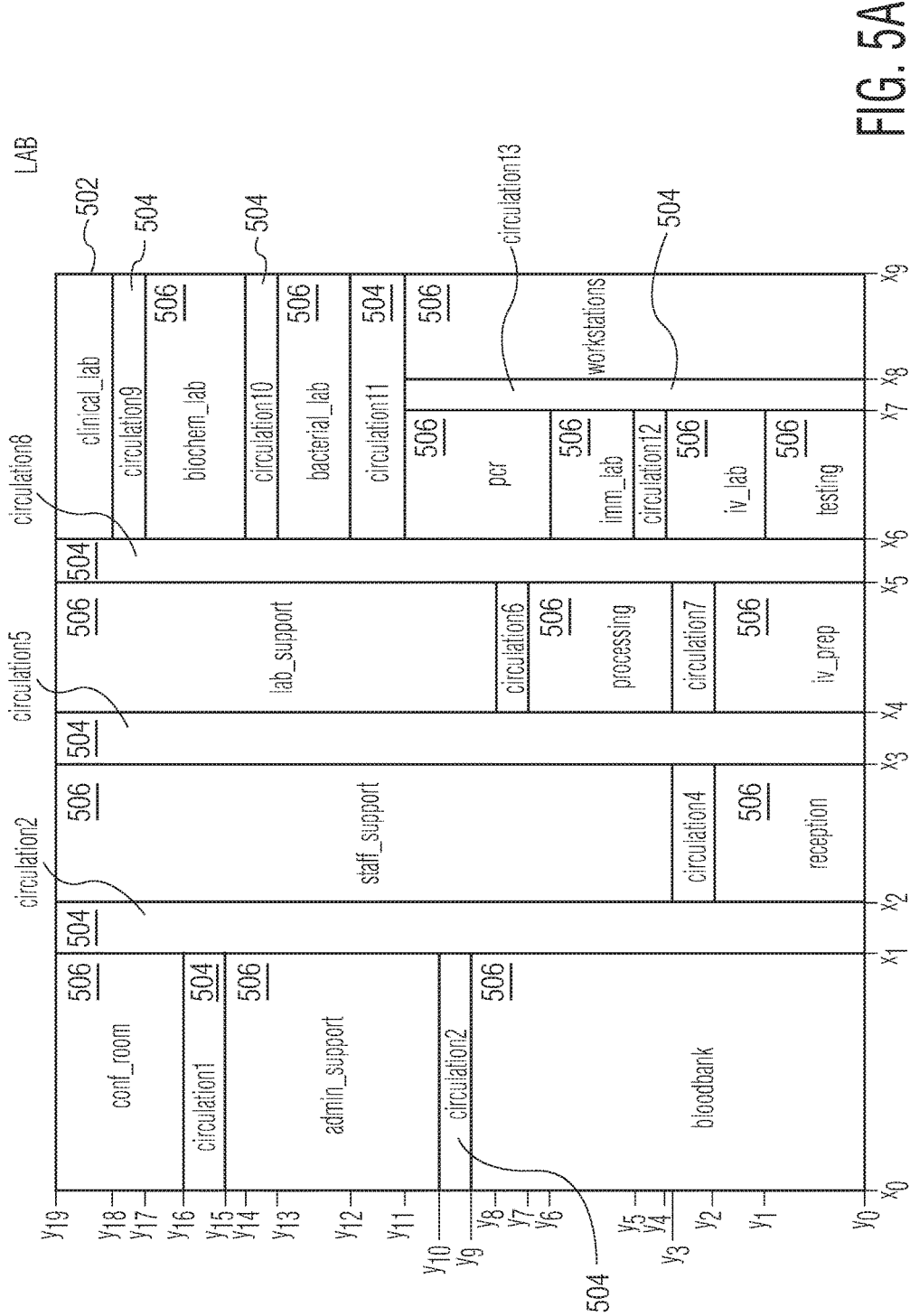
FIG. 5A depicts an example building floor plan with an architectural parti for a laboratory that includes a rectangular perimeter and a circulation pattern that includes multiple circulation elements (e.g., a pattern of horizontal and vertical corridors).

FIG. 5A depicts an example building floor plan with an architectural parti for a laboratory that includes a rectangular perimeter 502 and a circulation pattern that includes multiple circulation elements 504 (e.g., a pattern of horizontal and vertical corridors). FIG. 5A also depicts the placement of function-specific blocks 506 within the building relative to the circulation pattern. In an embodiment, the function-specific blocks are placed by an architectural planner without concern for the relative areas of the circulation elements and function-specific blocks and without concern for the aspect ratios of the circulation patterns and the function-specific blocks. As shown in FIG. 5A, circulation elements include circulation elements 1-13 (identified as "circulation1"-"circulation 13"), which are interconnected to define the circulation pattern. As shown in FIG. 5A, the function specific blocks include administration support (admin_support), bacterial lab (bacterial_lab), biochemical lab (biochem_lab), blood bank (bloodbank), clinical lab (clinical_lab), conference room (conf_room), human immunodeficiency virus (HIV) lab (hiv_lab), immunization lab (imm_lab), intravenous delivery prep (iv_prep), lab support (lab_support), polymerase chain reaction lab (per), processing, reception, staff support (staff_support), testing, and workstations.

In an embodiment, the circulation elements and function-specific blocks are placed within the building floor plan manually by an architectural planner without concern for the actual area (e.g., in terms of square footage) of the circulation elements and of the function-specific blocks and without concern for the aspect ratios of the circulation elements and of the function-specific blocks. In an embodiment, the manual placement may be made by, for example, hand drawing and/or a basic drawing program. An important consideration of the architectural planner in the placement process is the workflow between the function-specific blocks. For example, in the case of FIG. 5A, the workflow makes it desirable to have both of the operating room blocks (or1 and or2) relatively close to the support blocks (support1 and support2) and desirable to have the courtyard blocks (courtyard1 and courtyard2) relatively close to the operating room blocks (or1 and or2). Traditionally, the architectural planner utilizes personal experience and knowledge about workflow to place the function-specific blocks within a given architectural parti.

Figure 5B:
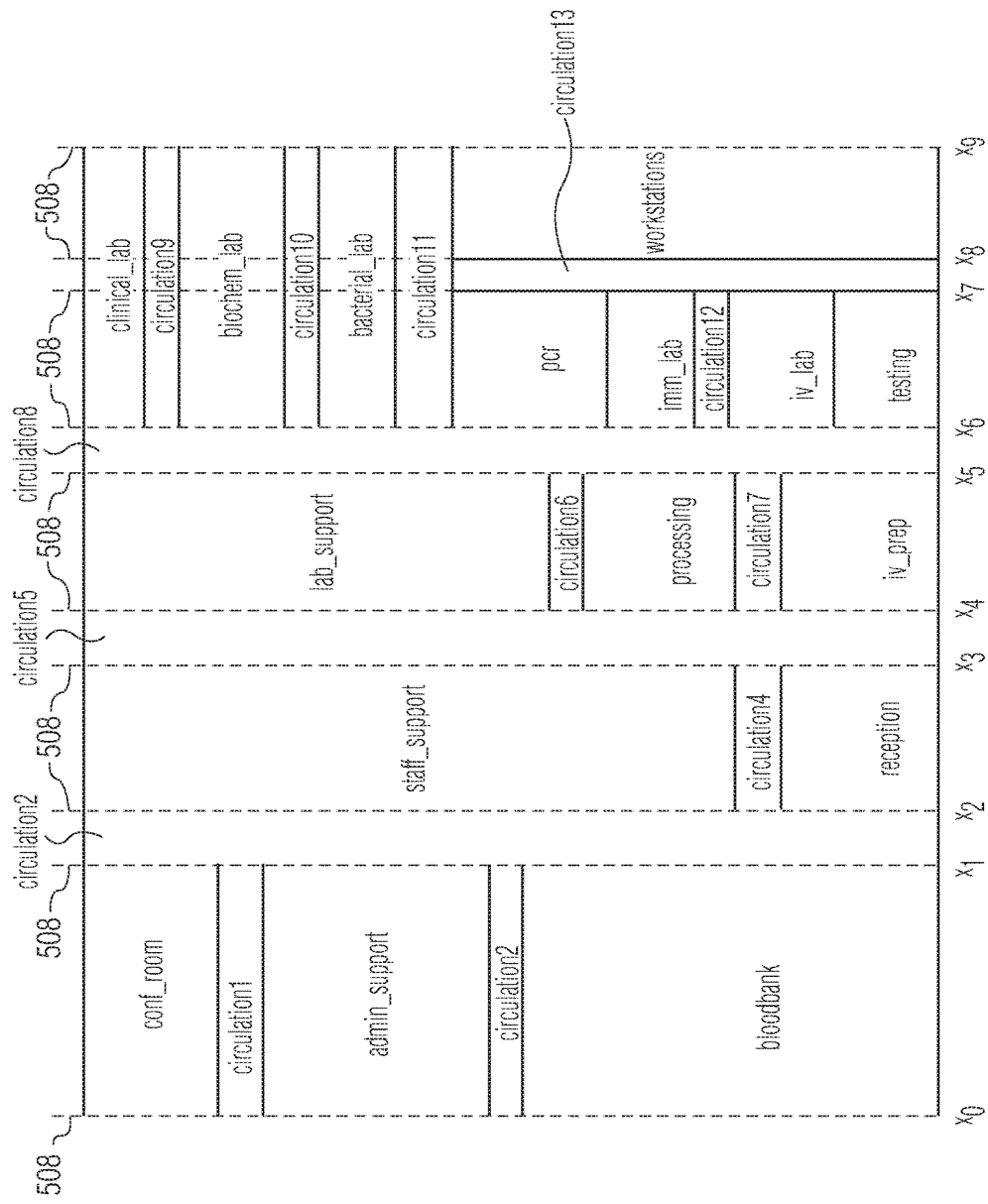
FIG. 5B illustrates the x-axis block edges that exist in the building floor plan of FIG. 5A.

Once the circulation elements and the function-specific blocks have been placed within the building floor plan, the relative locations of the circulation elements and the function-specific blocks are described using an x-y coordinate system. In an embodiment, a first step in the description process involves identifying each of the block edges along the x-axis, where edges exist at the vertical edge of any circulation element and at the vertical edge of any function-specific block. FIG. 5B illustrates the x-axis block edges 508 that exist in the layout of FIG. 5A. As illustrated in FIG. 5B, the block edges along the x-axis are identified by dashed vertical lines and include edges at coordinates x0-x9. At this point, the coordinates x0-x9 correspond to the block edges, but do not represent absolute values along the x-axis.

Figure 5C:
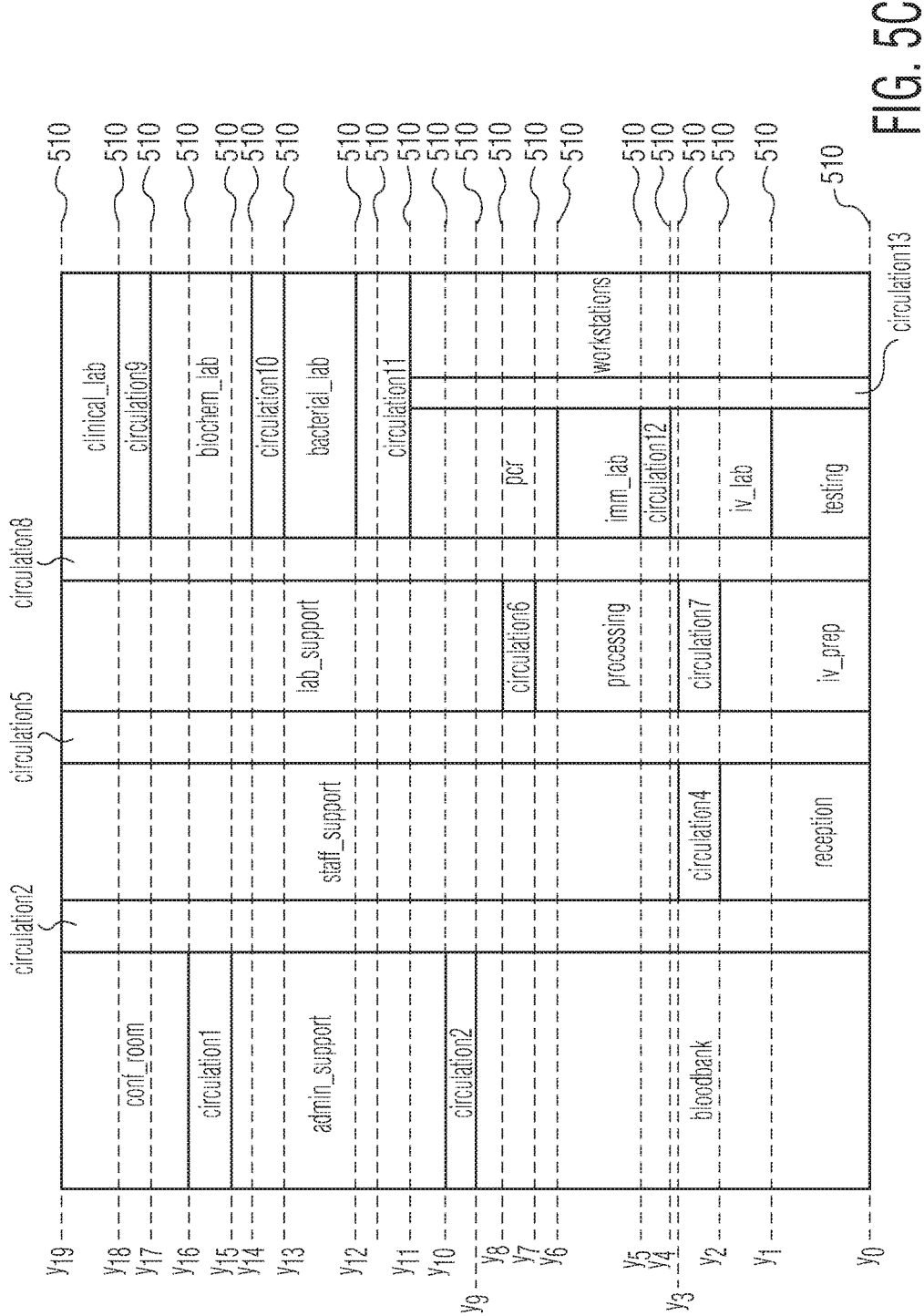
FIG. 5C illustrates the y-axis block edges that exist in the building floor plan of FIG. 5A.

A next step in the description process involves identifying each of the block edges along the y-axis, where a block edge exists at the horizontal edge of any circulation element and at the horizontal edge of any function-specific block. FIG. 5C illustrates the y-axis block edges 510 that exist in the building floor plan of FIG. 5A. As illustrated in FIG. 5C, the block edges along the y-axis are identified by dashed horizontal lines and include edges at coordinates y0-y19. As with the x-axis, at this point, the coordinates y0-y19 correspond to the block edges but do not represent absolute values along the y-axis.

The next step in the process involves describing the area of each circulation element and function-specific block using the coordinates of the identified block edges. In an embodiment, the process involves identifying circulation elements and function-specific blocks with a handle and associating the handles with coordinates of the corresponding vertices that represent the area of the respective circulation elements and function-specific blocks.

In an embodiment, the specifics of a particular building floor plan are modeled using a constraint-based programming language such as "MiniZinc" and stored in a file such as an ".mzn" file. In an embodiment, a base or generic parti can be modeled and stored in a base .mzn file and custom information for a specific parti can be modeled and stored in a custom .mzn file.

In an embodiment, the custom constraints file also includes a space program that identifies area requirements of some of the function-specific blocks.

With the desired knowns, unknowns, and constraints identified, the problem can be solved using an existing solver engine. In an embodiment, two different runs, run1 and run2, are provided using the same architectural parti. In run1, the maximum x dimension is constrained to be the same as the maximum y dimension and in run2 the maximum x dimension is constrained (e.g., xmax=40000). Outputs of the solutions are stored in a .yaml file.

Figure 5D:
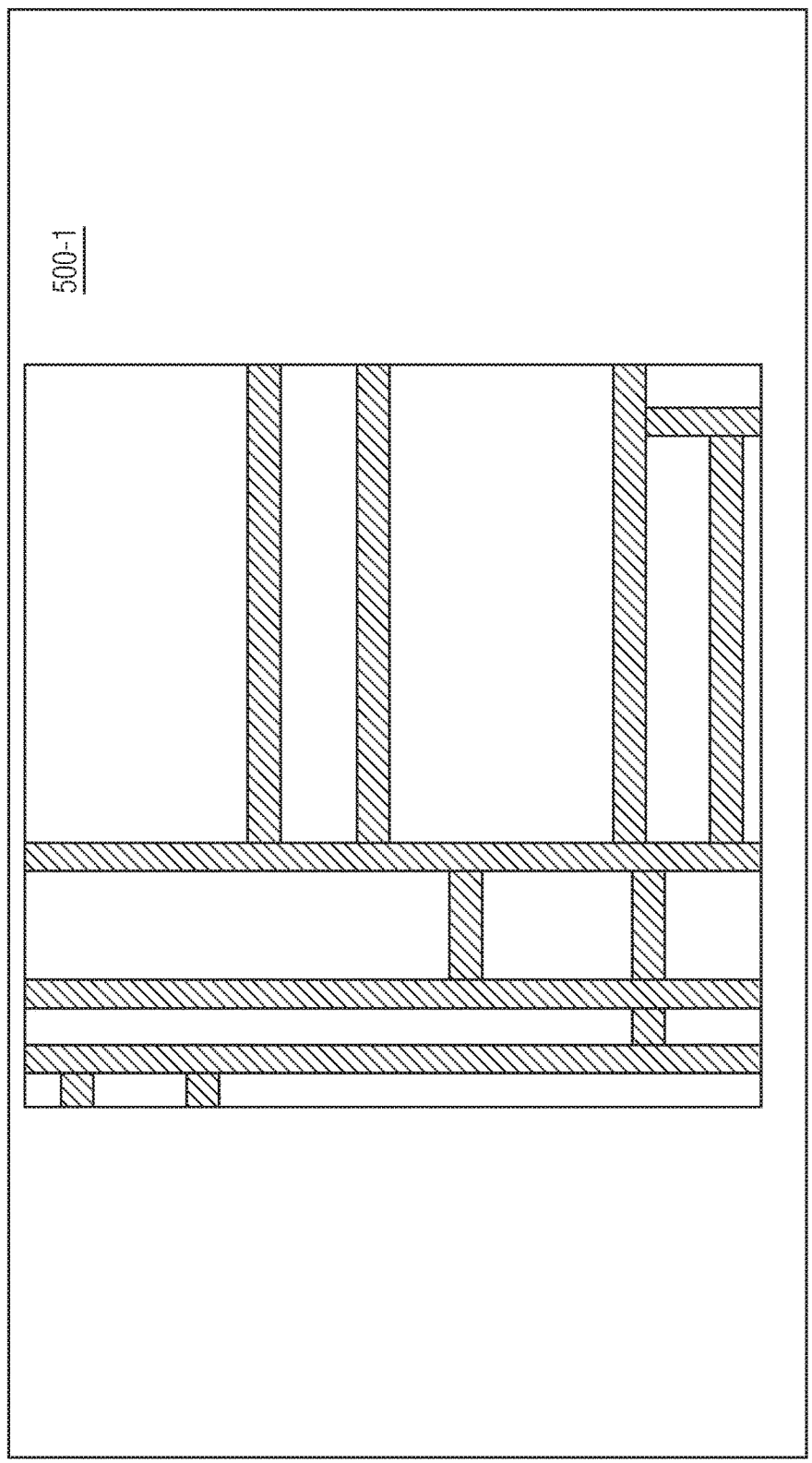
FIG. 5D is a graphical depiction of the run1 result as a floor plan layout.

FIG. 5D is a graphical depiction of the run1 result 500—1 as a floor plan layout.

Figure 5E:
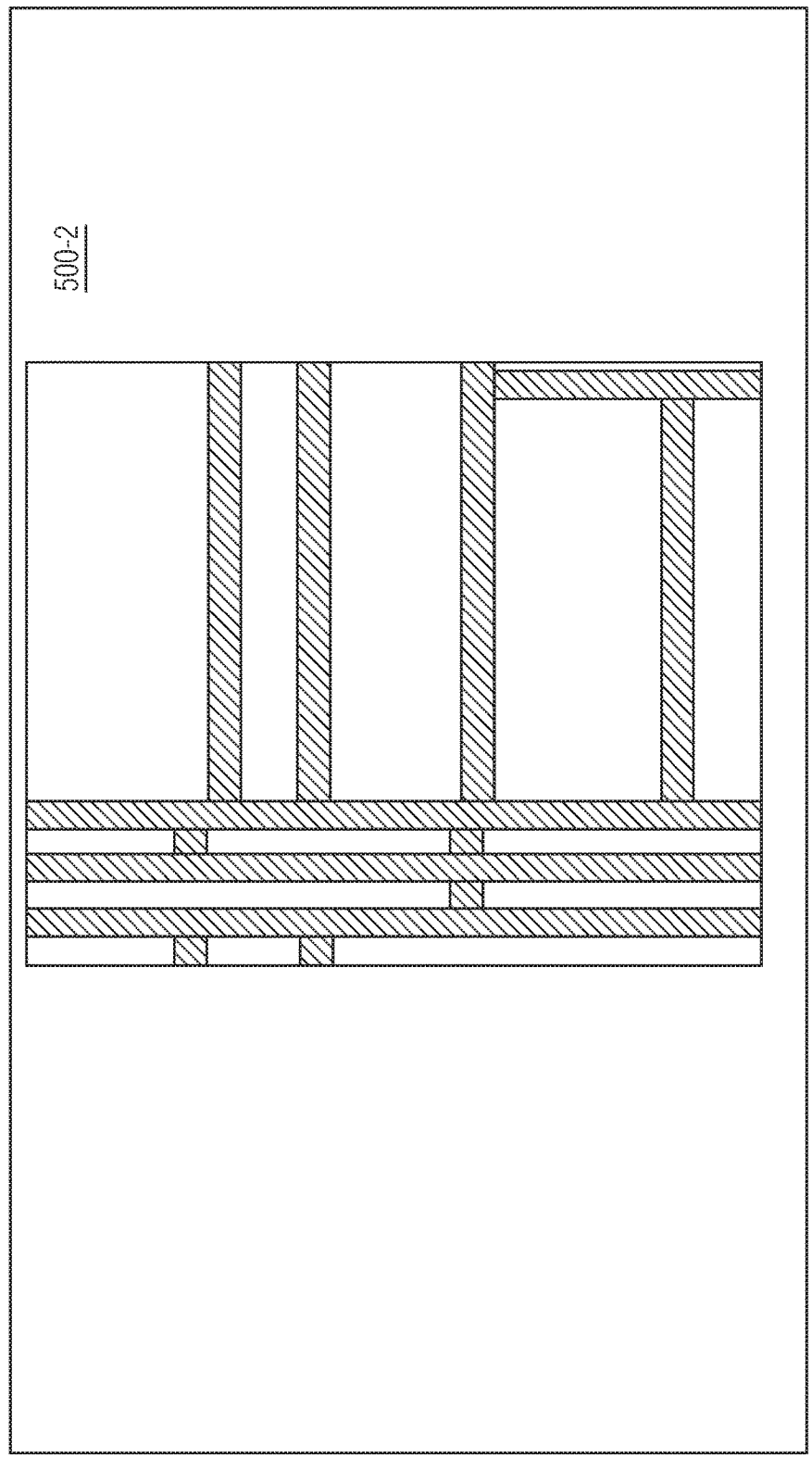
FIG. 5E is a graphical depiction of the run2 result as a floor plan layout.

FIG. 5E is a graphical depiction of the run2 result 500—2 as a floor plan layout.

System for Right-Sizing

The technique for right-sizing function-specific blocks is described above for two different healthcare departments (e.g., an operating room and a laboratory) with a specific architectural parti being used in each case. In an embodiment, the above-described technique is applied at a system level to provide a tool that can be used to right-size space programs using a library of previously modeled architectural partis.

In an embodiment, the library of architectural parti models can be populated with any number of different parti models. The different architectural parti models can represent the same department (e.g., an operating room) using different floor plan arrangements and/or different circulation patterns (e.g., different architectural partis) and/or could represent different departments with each department having a variety of different possible architectural partis. In an embodiment, an architectural parti model includes an architectural parti (e.g., a perimeter shape and circulation pattern) and a set of function-specific blocks already placed within the building. For example, one architectural parti model for an operating room would be stored as an .mzn file that represents the operating room of FIG. 4B and another architectural parti model for a laboratory would be stored as an .mzn file that represents the laboratory of FIG. 5B.

In operation, a user of the tool could select an architectural parti model for the desired department and architectural parti (e.g., as represented in a .mzn file) and find a right-sized floor plan layout given a particular space program. The process can be easily and quickly repeated for different space programs, for different architectural parti models, and for different constraints. Thus, the tool provides an architectural planner a quick and easy way to generate floor plan layouts.

Figure 6:
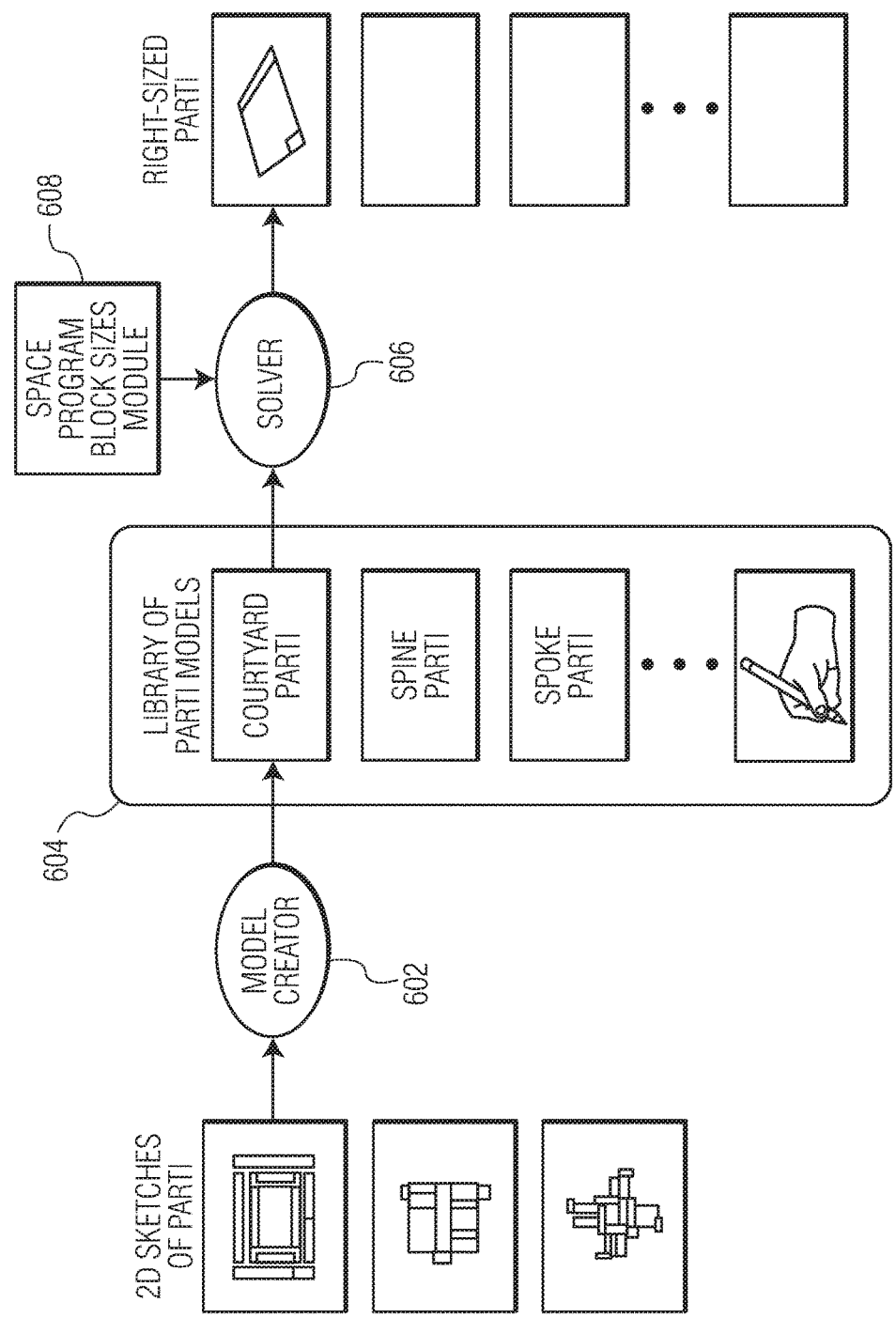
FIG. 6 is a functional block diagram of a right-sizing tool.

FIG. 6 is a functional block diagram of a right-sizing tool. In the embodiment of FIG. 6, the right-sizing tool includes a model creator 602, a library of architectural parti models 604, a solver 606, and a space program block sizes module 608. In an embodiment, a library of architectural parti models is created using the model creator. In an embodiment, models are created as described above with reference to FIGS. 4A-4C and FIGS. 5A-5C. In an embodiment, the space program block sizes module holds a space program that identifies the sizes, typically as an area (e.g., in square feet), of the function-specific blocks of a space program (see, for example, the space program of Table 1). In operation, a user selects an architectural parti model from the library and directs the solver to apply a particular space program to the model. The output of the application includes values for the x and y variables, which translate directly to the positions and areas of the circulation elements and of the function-specific blocks and to values for the aspect ratios of the circulation elements and the function-specific blocks. In an embodiment, the output of the solver is provided as a .yaml file. The output of the solver can also be translated to a graphic of the floor plan layouts as shown in FIGS. 4D, 4E, 5D, and 5E.

Figure 7:
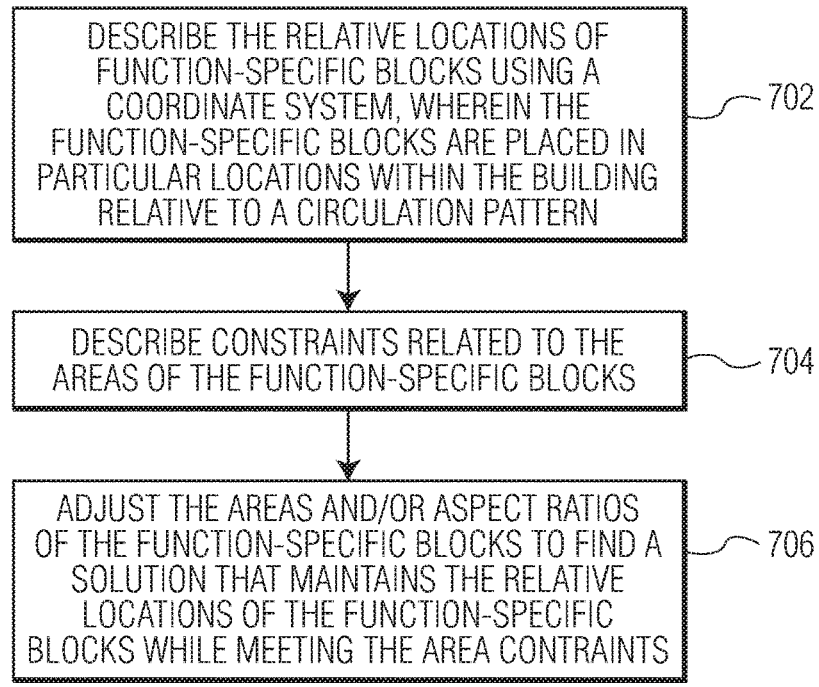
FIG. 7 is a flow chart diagram of a technique for right-sizing function-specific blocks in a healthcare building with a given architectural parti to support a specific space program in accordance with an embodiment of the invention.

FIG. 7 is a flow chart diagram of a technique for right-sizing function-specific blocks in a healthcare building with a given architectural parti to support a specific space program in accordance with an embodiment of the invention. At block 702, the relative locations of function-specific blocks are described using a coordinate system. In an embodiment, the function-specific blocks are placed in particular locations within the building relative to a circulation pattern. At block 704, constraints related to the areas of the function-specific blocks are described. At block 706, the areas and/or aspect ratios of the function-specific blocks are adjusted to find a solution that maintains the relative locations of the function-specific blocks while meeting the area constraints.

Figure 8:
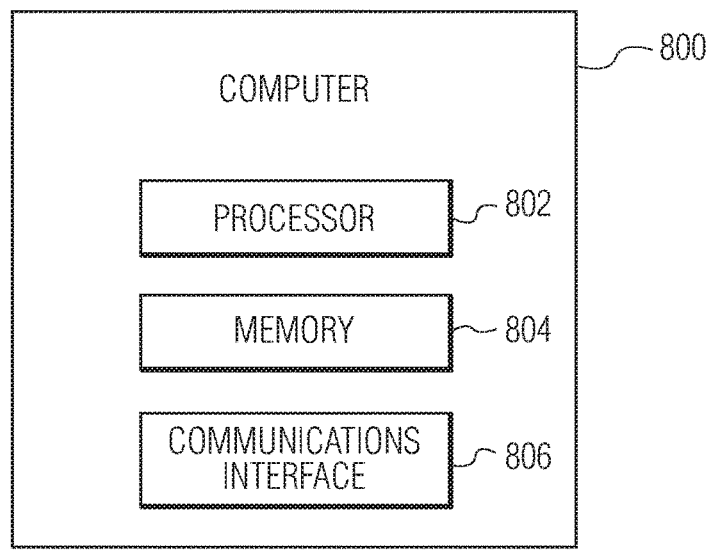
FIG. 8 depicts a computer that includes a processor, memory, and a communications interface.

In an embodiment, the above-described functionality, including functionality performed by the room placer tool, is performed by a computer or computers, which executes computer readable instructions. FIG. 8 depicts a computer 800 that includes a processor 802, memory 804, and a communications interface 806. The processor may include a multifunction processor and/or an application-specific processor. Examples of processors include the PowerPC™ family of processors by IBM and the x86 family of processors by Intel such as the Xeon™ family of processors and the Intel X5650 processor. The memory within the computer may include, for example, storage medium such as read only memory (ROM), flash memory, RAM, and a large capacity permanent storage device such as a hard disk drive. The communications interface enables communications with other computers via, for example, the Internet Protocol (IP). The computer executes computer readable instructions stored in the storage medium to implement various tasks as described above.

It will be readily understood that the components of the embodiments as generally described herein and illustrated in the appended figures could be arranged and designed in a wide variety of different configurations. Thus, the detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment. Rather, language referring to the features and advantages is understood to mean that a specific feature, advantage, or characteristic described in connection with an embodiment is included in at least one embodiment. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment. Thus, the phrases "in one embodiment," "in an embodiment," and similar language throughout this specification may, but do not necessarily, all refer to the same embodiment.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

It should also be noted that at least some of the operations for the methods may be implemented using software instructions stored on a computer useable storage medium for execution by a computer. As an example, an embodiment of a computer program product includes a computer useable storage medium to store a computer readable program that, when executed on a computer, causes the computer to perform operations, as described herein.

Furthermore, embodiments of at least portions of the invention, including the room placer tool, can take the form of a computer program product accessible from a computer-usable or computer-readable medium providing computer executable instructions, or program code, for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

The computer-useable or computer-readable medium can be an electronic, magnetic, optical, electromagnetic, infrared, or semiconductor system (or apparatus or device). Examples of a computer-readable medium include a semiconductor or solid state memory, magnetic tape, a removable computer diskette, a random access memory (RAM), a read-only memory (ROM), a rigid magnetic disk, and an optical disk. Current examples of optical disks include a compact disk with read only memory (CD-ROM), a compact disk with read/write (CD-R/W), and a digital video disk (DVD).

In the above description, specific details of various embodiments are provided. However, some embodiments may be practiced with less than all of these specific details. In other instances, certain methods, procedures, components, structures, and/or functions are described in no more detail than to enable the various embodiments of the invention, for the sake of brevity and clarity.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. A computer-implemented method for right-sizing function-specific blocks in a healthcare building with a given architectural parti to support a specific space program, the method comprising:
   describing relative locations of function-specific blocks using a coordinate system, wherein the function-specific blocks are placed in particular locations within a building relative to a circulation pattern;
   describing constraints related to areas of the function-specific blocks; and
   adjusting the areas and/or aspect ratios of the function-specific blocks to find a solution that maintains the relative locations of the function-specific blocks while meeting the area constraints;
   wherein describing the relative locations of function-specific blocks using a coordinate system involves identifying circulation elements and function-specific blocks with a handle and associating the handle with coordinates of corresponding vertices representing the area of the circulation elements and function-specific blocks.

2. The computer-implemented method of claim 1, wherein adjusting the areas and/or aspect ratios of the function-specific blocks comprises maintaining the circulation pattern.

3. The computer-implemented method of claim 1, wherein the function-specific blocks are placed in particular locations within the architectural parti of the building taking into account workflow of services that are provided within the function-specific blocks.

4. The computer-implemented method of claim 1, wherein the handle is associated with a range of coordinates.

5. The computer-implemented method of claim 1, further comprising outputting the solution as x and y variables that translate directly to the positions, areas, and aspect ratios of function-specific blocks.

6. The computer-implemented method of claim 1, further comprising outputting a graphical depiction of the solution that includes the adjusted areas and/or aspect ratios.

7. A computer-implemented method for right-sizing function-specific blocks in a healthcare building with a given architectural parti to support a specific space program, the method comprising:
   identifying knowns related to function-specific blocks that are placed in particular locations within a building relative to a circulation pattern;
   identifying unknowns related to the function-specific blocks as placed within the building relative to the circulation pattern;
   identifying constraints related to the function-specific blocks as placed within the building relative to the circulation pattern; and
   solving for the unknowns given the knowns and the constraints to adjust areas and/or aspect ratios of the function-specific blocks to find a solution that maintains the relative locations of the function-specific blocks while meeting the area constraints;
   wherein describing the relative locations of function-specific blocks using a coordinate system involves identifying circulation elements and function-specific blocks with a handle and associating the handle with coordinates of corresponding vertices representing the area of the circulation elements and function-specific blocks.

8. The computer-implemented method of claim 7, wherein adjusting the areas and/or aspect ratios of the function-specific blocks comprises maintaining the circulation pattern.

9. The computer-implemented method of claim 7, wherein the function-specific blocks are placed in particular locations within the architectural parti of the building taking into account workflow of services that are provided within the function-specific blocks.

10. The computer-implemented method of claim 7, wherein adjusting the areas and/or aspect ratios of the function-specific blocks involves directing a solver to apply a particular space program to a previously modeled architectural parti having the same identified knowns.

11. The computer-implemented method of claim 10, wherein the previously modeled architectural parti is selected from a library that includes at least one previously modeled architectural parti for at least one department using at least one building floor plan.

12. The computer-implemented method of claim 7, further comprising outputting the solution as x and y variables that translate directly to positions, areas, and aspect ratios of function-specific blocks.

13. The computer-implemented method of claim 7, further comprising outputting a graphical depiction of the solution that includes the adjusted areas and/or aspect ratios.

14. A computer-implemented method for right-sizing function-specific blocks in a healthcare building with a given architectural parti to support a specific space program, the method comprising:
   identifying knowns related to function-specific blocks that are placed in particular locations within a building relative to a circulation pattern;
   identifying unknowns related to the function-specific blocks as placed within the building relative to the circulation pattern;
   identifying constraints related to the function-specific blocks as placed within the building relative to the circulation pattern;
   solving for the unknowns given the knowns and the constraints to adjust areas and/or aspect ratios of the function-specific blocks to find a solution that maintains the relative locations of the function-specific blocks while meeting the area constraints; and
   outputting the solution as x and y variables that translate directly to positions, areas, and aspect ratios of function-specific blocks.

15. The computer-implemented method of claim 14, wherein adjusting the areas and/or aspect ratios of the function-specific blocks comprises maintaining the circulation pattern.

16. The computer-implemented method of claim 14, wherein the function-specific blocks are placed in particular locations within the architectural parti of the building taking into account workflow of services that are provided within the function-specific blocks.

17. The computer-implemented method of claim 14, wherein describing the relative locations of function-specific blocks using a coordinate system involves identifying circulation elements and function-specific blocks with a handle and associating the handle with coordinates of corresponding vertices representing the area of the circulation elements and function-specific blocks.

18. The computer-implemented method of claim 14, wherein adjusting the areas and/or aspect ratios of the function-specific blocks involves directing a solver to apply a particular space program to a previously modeled architectural parti having the same identified knowns.

19. The computer-implemented method of claim 18, wherein the previously modeled architectural parti is selected from a library that includes at least one previously modeled architectural parti for at least one department using at least one building floor plan.

20. A computer-implemented method for right-sizing function-specific blocks in a healthcare building with a given architectural parti to support a specific space program, the method comprising:
   describing relative locations of function-specific blocks using a coordinate system, wherein the function-specific blocks are placed in particular locations within a building relative to a circulation pattern;
   describing constraints related to areas of the function-specific blocks;
   adjusting the areas and/or aspect ratios of the function-specific blocks to find a solution that maintains the relative locations of the function-specific blocks while meeting the area constraints; and
   outputting the solution as x and y variables that translate directly to the positions, areas, and aspect ratios of function-specific blocks.

* * * * *